United States Patent

Simmet

(10) Patent No.: US 6,596,472 B2
(45) Date of Patent: Jul. 22, 2003

(54) REPRODUCTIVE CULTURES CONTAINING COLLOIDAL SILVER

(75) Inventor: Ludwig O. Simmet, Verona, WI (US)

(73) Assignee: Minitube of America, Inc., Verona, WI (US)

( * ) Notice: Subject to any disclaimer, the term of this patent is extended or adjusted under 35 U.S.C. 154(b) by 0 days.

(21) Appl. No.: 09/883,136

(22) Filed: Jun. 14, 2001

(65) Prior Publication Data

US 2002/0022214 A1 Feb. 21, 2002

Related U.S. Application Data

(60) Provisional application No. 60/219,347, filed on Jun. 14, 2000.

(51) Int. Cl.$^7$ .................. A61K 35/48; A61K 35/52; A61K 35/54; A61K 33/38
(52) U.S. Cl. .................. 435/2; 435/374; 424/561; 424/582; 424/618
(58) Field of Search .................. 424/520, 561, 424/581, 582, 600, 618; 435/2, 325, 374, 618, 520, 561, 600, 582

(56) References Cited

FOREIGN PATENT DOCUMENTS

| DE | 1981-63659D | * | 12/1980 |
| DE | 1982-03550 E | * | 4/1981 |
| JP | 01107755 A | * | 4/1989 |

OTHER PUBLICATIONS

Chen et al., "Survival of bull spermatozoa seeded and frozen at different rates in egg yolk–tris and whole milk extenders", J Dairy Science, Apr. 1993 76 (4):1028–34.*

Chen et al., "Survival of bull spermatozoa seeded and frozen at different rates in egg yolk–tris and whole milk extenders", J Dairy Science, Apr. 1993 76 (4):1028–34.*

1999 Web Article written by Marvin Robey http://www.colloidal–silver.com/whatiscsinfo.htm, Copyright© 1999, Colloidal Silver Discovery Center.

* cited by examiner

*Primary Examiner*—Leon B. Lankford Jr.
*Assistant Examiner*—Ruth A. Davis
(74) *Attorney, Agent, or Firm*—Lathrop & Clark LLP

(57) ABSTRACT

A colloidal dispersion of nanoparticles of silver is used to preserve animal reproductive samples such as boar semen without the use of antibiotics. The colloidal silver solution may have a metal concentration of at least about $1 \times 10^{-9}$ moles/liter and may be mixed with conventional culture media such as semen extender.

6 Claims, No Drawings

REPRODUCTIVE CULTURES CONTAINING COLLOIDAL SILVER

CROSS REFERENCES TO RELATED APPLICATIONS

This application claims priority on U.S. provisional application No. 60/219,347, filed on Jun. 14, 2000, the disclosure of which is incorporated by reference herein.

STATEMENT AS TO RIGHTS TO INVENTIONS MADE UNDER FEDERALLY SPONSORED RESEARCH AND DEVELOPMENT

BACKGROUND OF THE INVENTION

A substantial proportion of the swine produced in North America today are produced utilizing artificial insemination. Thus, the ability to preserve animal reproductive samples, such as semen, oocytes and embryos, for use in artificial insemination and other reproductive processes is important. Without this ability, it is not possible to transport animal reproductive samples or store the samples for any length of time; thus, the utility of the samples is limited.

To protect reproductive samples from bacterial contamination, it has been common practice to introduce antibiotics into the preservation mediums or extender solutions. Although conventional antibiotics can be a low cost and effective way of preserving the samples, there are long term consequences of the continued widespread use of antibiotics. Over time, bacteria come to the fore which are resistant to antibiotics. The presence of low levels of antibiotics in agricultural livestock and human food products is considered to be one cause of the increasingly resistant bacteria. The increased resistance of bacteria to antibiotics poses a danger to humans and animals as infectious diseases are becoming more difficult to treat. Hence, in certain regions, conventional antibiotics are no longer effective. Moreover, there is consideration being given by regulatory bodies to banning the general use of antibiotics in animals raised for food production. Thus, it is desirable to have an extender that has antimicrobial properties, but is substantially free of antibiotics. It is also desirable to have a method for preserving animal reproductive samples that uses an extender that has antibicrobial properties, but is substantially free of antibiotics.

SUMMARY OF THE INVENTION

The method of this invention mixes a colloidal suspension of silver as a component of a preservation medium for the preservation of animal reproductive samples. By adding the colloidal suspension of silver to conventional semen extenders, for example, an extender for boar semen which has antimicrobial properties, but substantially free of antibiotics is produced. A colloidal silver solution having a silver concentration of at least about $1 \times 10^{-9}$ moles/liter has been found effective in preserving some reproductive materials.

It is an object of the present invention to provide an extender with antibacterial and antiviral properties without the use of antibiotics.

Further objects, features and advantages of the invention will be apparent from the following detailed description when taken in conjunction with the accompanying drawings.

BRIEF DESCRIPTION OF THE DRAWINGS

Not applicable.

DESCRIPTION OF THE PREFERRED EMBODIMENTS

A colloidal dispersion of nanoparticles of silver may be used to preserve reproductive samples such as boar semen, producing a medium which is antibacterial and antiviral. The colloidal dispersion of silver may be produced through the methods detailed below, or any other suitable method. In particular, a colloidal silver solution is mixed with an extender concentrate to form an extender composition. The colloidal silver solution has a silver concentration of at least about $1 \times 10^{-9}$ moles/liter. The silver may be present in one or more forms, including ionic, elemental, or a mixture thereof. Further, the ions may be present in one or more oxidation states. The silver ions have an affinity to sulfhydryl groups in enzyme systems, and through which they interfere with the transmembraneous energy transfer in bacterial microorganisms.

For example, the extender concentrate may be BTS which is sold by a number of manufacturers, Androhep® which is manufactured by Minitube of America, Verona, Wis.; Acromax which is sold by Continental Plastics Corp., Delavan, Wis., or Vital, VSP or X-Cell™ which are manufactured by I.M.V. International Corp., Minneapolis, Minn. The extender composition is formed by mixing the extender concentrate as directed by the manufacturer of the concentrate, substituting the colloidal silver suspension for the water.

The extender composition is then mixed with an animal reproductive sample to form a biological culture medium useful for animal reproduction. The animal reproductive sample is typically semen, oocytes, embryos or other solutions usable for reproductive purposes. Preferably, the animal reproductive sample is boar semen. The concentration and viability of the animal reproductive sample is determined by known methods in the art. Based on the concentration and viability of the animal reproductive sample, an amount of the extender composition is added to maximize the number of doses of the biological culture medium useful for animal reproduction. The amount of extender composition to be added to the animal reproductive sample is determined based on traditional methods in the art.

As is well known, the chemical composition of animal reproductive samples will vary from animal to animal, and even between collections from the same animal. Excessive levels of chlorine or nitrogen in the sample, for example boar semen, will form compounds with the silver solution which are detrimental to the effectiveness of the extender, and at times even spermicidal. Hence, the extender composition of the present invention should not be used where chlorine concentrations are more than about 700 ppm. Likewise, if the nitrogen levels in the animal reproductive sample are too high, the extender composition of the present invention does not work.

The biological culture medium of the present invention is microbiologically stable at refrigerated conditions (less than about 40° F.) for up to one week.

Colloidal suspensions of silver are antimicrobial as shown below in Table 1. Bacterial contaminated water solutions were prepared and treated either by processing through a dense media plasma reactor or by adding a solution that was processed through a dense media plasma reactor. The bacterial contaminated water solutions and the plate counts of surviving bacteria have been carried out at the Food Research Institute-UW according to the following procedure:

Inoculum for Water Contamination:

Four bacterial strains were grown overnight in trypticase soy broth (TSB) at room temperature. The next day they were transferred to TSB (diluted 1:100 in distilled water) and grown overnight at room temperature. The stains were pooled and inoculated into water from Aldrich Chemical Co. (32,007-2 ACS grade).

Bacterial stains used were two *Pseudomonas fluorescens*; a *Salmonella typhimurium* and an *Etrobacter agglomerans*.

Procedure for Testing Survival of Bacteria:

Bacteria-contaminated water solutions were treated under the DMP-plasma conditions for different time intervals (Table 1).

After plasma-treatment, the samples were directly plated or diluted in phosphate buffered saline and then plated on Trypticase soy agar. The plated were incubated at room temperature for 72 hours. To test for injured bacteria, 0.5 ml of each sample was added to 4.5 ml of SB and incubated at room temperature.

In all solutions resulting from the plasma-treatments the bacteria were totally killed. Even solutions prepared from 200 ml, initial "living-bacterial soup" and 1 ml of solution of the 10 seconds plasma-treated bacterial soup exhibited a 99% reduction of the living bacterial content. The only samples that were positive for growth upon enrichment were the untreated water and untreated water with 1 ml of 10 seconds treated bacterial soup.

Treatment of the samples, even for 5 seconds, killed the bacterial inoculum. No bacteria were recovered either by direct plate count or by enrichment. Addition of the 10 second treated bacterial solution to the untreated inoculated water efficiently reduced the bacterial count by 98:1.

Survival Results

TABLE 1

Antimicrobial Activity of Colloidal Silver Dispersion

| # | Sample | DC voltage (V) | DC current (A) | Time(s) | Plate Counts of surviving bacteria (log CFU/ml) | Plate counts of surviving bacteria (CF U/ml) |
|---|---|---|---|---|---|---|
| C.S. 1 | Initial inoculum of water | — | — | — | 5.73 | 537,032 |
| C.S. 2 | Water held until treated samples were plated | — | — | — | 5.41 | 257,040 |
| Ex. A | Bacteria samples treated for 5s | 200 | 0.4 | 5 | <1.0 | 0 |
| Ex. B | Bacteria sample treated for 10s | 200 | 0.4 | 10 | <1.0 | 0 |
| Ex. C | Bacterial sample treated for 1 min | 200 | 0.4 | 60 | <1.0 | 0 |
| Ex. D | Water ACS treated and added 1:1 to bacteria sample | 200 | 0.4 | 60 | <1.0 | 0 |
| Ex. E | 1 ml of bacteria sample treated for 10 s added to 200 ml untreated bacteria sample | — | — | — | 3.69 | 4,898 |

Minimizing the silver particle sizes is believed to be important both from the stability of the colloidal suspension and for the efficacy against microbes. Various processes to produce nanoparticles are known. For example, those disclosed in U.S. Pat. Nos. 5,543,133; 5,585,020; 5,879,750; and 6,540,495. CS Pro Systems advertises a high voltage AC processor producing nanoparticles of colloidal metal. The HVAC process is claimed to produce particle sizes between 0.002 to 0.007–9 microns by imposing an AC potential of 10,000 volts across two metal electrodes in a distilled water medium.

Colloidal suspensions of nanoparticles of electrically conductive materials can also be produced by generating a plasma reaction between two electrodes, comprising the desired electrically conductive material(s), which are immersed within a dense fluid medium. Preferably, the dense medium is rapidly recirculated between the two electrodes.

The colloidal nanoparticle dispersion is produced by fine sputtering particles of the electrically conducting material from the electrodes, by the multitudes of (DC or AC) discharges initiated and sustained between the rotating and the stationary electrodes, into the intensely stirred dense medium, which is preferably water.

For the present invention, the electrodes are silver. Typically, the electrically conducting material should be at least about 90 percent pure, preferably at least about 95 percent pure, more preferably at least about 99 percent pure.

Preferably, the electrodes are constructed so as to be easily removed and installed. This easy interchangeability facilitates replacing worn electrodes or changing electrodes to accommodate the production of different colloidal dispersions.

The dense medium may be any liquid having a viscosity low enough to permit rapid circulation of the fluid between the two electrodes. The plasma reaction will decompose the molecules of the dense medium into highly reactive free radicals. As such, the reaction products formed from the dense medium free radicals may be undesirable contaminants to the colloidal solution. Preferably, the dense medium will not form undesirable by-products during the plasma reaction. An undesirable by-product is any compound that must be removed, due to technical, practical or aesthetic reasons, from the colloidal dispersion prior to use. In most cases, when inorganic/organic hybrid nanoparticle systems are prepared, liquid phase organometallic compounds can be used. The dense medium is typically selected to avoid the production of undesirable byproducts. In the preferred embodiment, the decomposition reaction products of water ($H^+$ and $OH^-$) readily react with each other to reform the water molecule. In contrast, the decomposition reaction products of other dense media, e.g. benzene, are free radicals which may initiate polymerization reactions.

The dense medium, and any by-product of the plasma reaction, should have, at most, a slow reaction rate with the electrically conductive material. Preferably, any reaction between the dense medium and the electrically conductive material is slow enough that the nanoparticles in the colloidal dispersion have the desired shelf-life. Most preferably, the dense medium, and any by-product, is non-reactive with the electrically conducting material. "Non-reactive" means that the dense medium and the nanoparticle material do not combine to form a new compound under the operating conditions of the plasma reactor. In the present invention the dense medium is water.

The electrodes and the dense fluid medium are located within any suitable containment means. The containment means may be open or closed, preferably closed, more preferably a closed pressure vessel. The containment means optionally has means, such as a vacuum pump, to evacuate the containment means. Preferably, the containment means may be pressurized, more preferably pressurized by charging the containment means with an overpressure of inert gas. Preferably, the containment means has means, such as ports, valve, pumps, etc., to charge and discharge the dense medium. The dimensions of the containment means should be sufficient to prevent loss of the dense medium or colloidal dispersion and to provide the volume required for the volume of dense medium and electrodes. Preferably, the containment means has a size and shape to accommodate the desired batch size/throughput rate of the dense medium such that the desired circulation pattern of the dense medium may be obtained without dead spots. Several containment means may be connected in parallel or, preferably, in series, to facilitate continuous production of the colloidal dispersion.

The colloidal dispersions of this invention are conveniently produced in dense medium plasma reactors. An example of such a reactor is disclosed in U.S. Pat. No. 5,534,232, which is incorporated herein by reference. However, one skilled in the art will recognize that any dense medium plasma reactor which comprises at least two electrodes, means for rapidly recirculating the dense medium between the two electrodes and means to provide bubbles within the dense medium circulating between the electrodes is suitable for use in this invention.

Preferably, the voltage applied across the electrode faces is in the range of 100 to 800 Volts, more preferably about 100 to about 250, most preferably about 200 V. The higher voltage peaks (e.g., 250–300 V) applied to the electrodes at the starting point (i.e., the first moment of voltage application) decreases to 100–250 V during the reaction, which is determined by the conductivity of newly synthesized compounds, and the DC current stabilizes between the limits of 0.1–4 Amps. This results in a power range of 101000 Watts. By establishing a low electric current to the electrode faces and rapidly rotating the upper planar electrode face relative to the lower planar electrode face without touching the stationary lower planar electrode face, the electric discharge or discharges are initiated in different locations of the plasma zone, i.e. different locations within the planar gap, thereby eluding the creation of local caloric energy concentrations. As a result, the reaction mechanisms produced from the inventive method and apparatus for forming nanoparticles of conducting particles are controlled by electron flux intensity rather than thermal energy.

The dense medium is preferably circulated between the upper and lower planar electrode faces because the plasma reaction and sputtering only occurs in the planar gap located between the electrode faces. The circulation of the dense medium results from the centrifugal force created by the rotation of the upper planar electrode face relative to the lower planar electrode face. This centrifugal force causes the dense medium located between the electrode faces to move radially outward (away from electrode faces). The radial outward movement of the dense medium creates vacuum and cavitation effects which draw more dense medium from within the reaction vessel through a plurality of ports located in the lower static electrode, into the hollow shaft of the electrode, and through the openings of the lower static electrode to the planar gap located between the electrode faces.

The rotation of the upper rotatable electrode also aids in circulating the dense medium contained within the reaction vessel. The same centrifugal force created by rotating the upper planar electrode face in relation to the lower planar electrode face causes some of the dense medium located in the planar gap between the electrode faces to gravitate into the lower portion of the reaction vessel. This gravitation of the dense medium subsequently forces the dense medium to recirculate from a lower site within the reaction vessel to an upper site within the reaction vessel via the reactant recirculation line and peristaltic pump which are part of the dense medium plasma reactor. In summary, the centrifugal force created by rotating the upper rotatable electrode induces a very intense movement and mixing of the dense medium. The rotation of the upper rotatable electrode permits the fast removal of active species from the plasma zone, i.e., that area which constitutes the planar gap located between the electrode faces, thereby inhibiting the development of extensive decomposition reactions. The rapid circulation also removes the nanoparticles from the area between the electrodes thereby decreasing the possibility of the nanoparticles reattaching to the electrodes. In addition, the rotation of the upper rotatable electrode aids in the achievement of a caloric energy equilibrium of the dense medium.

The finished colloidal dispersion of electrically conducting nanoparticles may be discharged from the dense medium plasma reactor by any convenient means. The small size of the nanoparticles permits the forces of Brownian motion to maintain the nanoparticles and dispersion rather than settling out of the dispersion.

The temperature of the system may be monitored and controlled by a thermostat.

The method for producing nanoparticles of electrically conducting materials by means of an induced plasma state may also be carried out as a continuous flow-system reaction. This can be achieved by selecting the proper residence times of dense media in the reactor and employing circulation means, e.g., a peristaltic pump, to circulate the dense medium in and out of the reaction vessel via input and output lines which are connected to the reaction vessel.

The continuous method for producing nanoparticles of electrically conducting materials may also be carried out in a multi-stage plasma reactor. Such a multi-stage plasma reactor comprises multiple dense medium plasma reactors as described above connected either in series or parallel, preferably in series. In the preferred series multi-stage reactor, the output of the upstream reactors is connected to the input of the downstream reactors. The rotating electrodes are all attached to a common shaft and therefore rotate at the same speed as each other.

The dense media is introduced to this multi-stage reactor through an inlet on the bottom of the reactor. The dense media flows through conduits in the first stage static electrode into the center area of the planar gap between the first stage static electrode and the first stage rotating electrode. The plasma reaction, electrode sputtering and dense media circulation occur within the first stage of the reactor as described above for the single stage plasma reactor. The dense media from the first stage of the plasma reactor, bearing an amount of the colloidal dispersion of nanoparticles comprising the electrically conducting material of the electrodes, exits the first stage and enters the second stage of the reactor through conduits in the second stage static electrode. The conduits in the second stage static electrode also introduce the dense media to the center of the planar gap between the second stage static electrode and the second stage rotating electrode. This process is repeated for each stage of the multi-stage reactor.

The finished colloidal dispersion of nanoparticles may be collected from the final stage of the multistage reactor. Conveniently, such collection is by means of an overflow discharge from the top of the last stage of the multistage reactor.

It is understood that the invention is not limited to the particular construction and arrangement of parts herein illustrated and described, but embraces all such modified forms thereof as come within the scope of the following claims.

I claim:
1. An extender composition for the preservation of animal reproductive samples, comprising:
   an extender concentrate; and
   a colloidal suspension of elemental silver or oxides thereof.
2. The extender composition of claim 1, wherein the colloidal suspension of silver has a silver concentration of at least about $1 \times 10^{-9}$ moles/liter.
3. A biological culture medium useful for animal reproduction, comprising:
   an extender concentrate;
   a colloidal suspension of elemental silver or oxides thereof; and
   an animal reproductive sample.
4. The biological culture medium of claim 3, wherein the colloidal suspension of silver has a silver concentration of at least about $1 \times 10^{-9}$ moles/liter.
5. The biological culture medium of claim 3, wherein the animal reproductive sample is selected from the group consisting of semen, oocytes and embryos.
6. A biological culture medium for the preservation of animal reproductive samples substantially free of antibiotics, comprising:
   an extender concentrate;
   a colloidal suspension of silver; and
   an animal reproductive sample, wherein the animal reproductive sample has a chlorine level of less than about 700 ppm.

* * * * *